(12) United States Patent
Lazeroms et al.

(10) Patent No.: US 9,987,484 B2
(45) Date of Patent: Jun. 5, 2018

(54) METHOD AND SYSTEM FOR LEAD DELIVERY

(75) Inventors: Markus J. C. Lazeroms, Vroehoven-Riemst (BE); Paulus G. Adams, Munstergeleen (NL)

(73) Assignee: Medtornic, Inc., Minneapolis, MN (US)

( * ) Notice: Subject to any disclaimer, the term of this patent is extended or adjusted under 35 U.S.C. 154(b) by 1797 days.

(21) Appl. No.: 13/460,944

(22) Filed: May 1, 2012

(65) Prior Publication Data
US 2013/0296879 A1 Nov. 7, 2013

(51) Int. Cl.
*A61B 19/00* (2006.01)
*A61N 1/05* (2006.01)
(Continued)

(52) U.S. Cl.
CPC ........ *A61N 1/0587* (2013.01); *A61B 17/3468* (2013.01); *A61B 2017/00561* (2013.01); *A61B 2017/00566* (2013.01); *A61B 2017/306* (2013.01); *A61B 2017/308* (2013.01); *A61B 2018/00273* (2013.01);
(Continued)

(58) Field of Classification Search
CPC ................ A61N 1/0587; A61N 1/0592; A61N 2005/0649; A61N 1/05; A61N 1/00358; A61N 1/057; A61N 1/0573; A61N 1/059; A61N 1/306; A61N 2001/058; A61M 1/00; A61M 1/0015; A61M 1/0009; A61M 25/04; A61B 2017/22021; A61B 2017/0237; A61B 2017/00243; A61B 2017/0243; A61B 2017/306; A61B 2017/308; A61B 2017/00561; A61B 2017/00566; A61B 5/150145; A61B 5/150152; A61B 5/15016; A61B 5/6834; A61B 5/6869; A61B 5/6879; A61B 5/04085; A61B 5/04485; A61B 5/6846; A61B 5/6847; A61B 5/6867; A61B 5/15; A61B 5/125; A61B 5/683; A61B 2018/00273; A61B 2018/00291; A61B 17/3468; A61B 1/00094; A61B 5/04082; A61B 5/0408; A61B 5/686; A61B 5/0055; A61B 2017/00247; A61B 2017/3425;
(Continued)

(56) References Cited

U.S. PATENT DOCUMENTS

5,313,943 A    5/1994 Houser et al.
5,336,252 A *  8/1994 Cohen .......................... 607/119
(Continued)

*Primary Examiner* — Jonathan Miles
*Assistant Examiner* — Kendra Obu (57) ABSTRACT

A system and method enables delivery of an implantable medical lead to an implant location. A delivery tool of the system defines the delivery angle of the lead at the implant location. The delivery tool includes an elongate body having at least one lumen extending from a distal portion to a proximal portion. A suction cup is coupled to the distal portion of the elongate body. The suction cup may be configured to be collapsible in a first configuration, prior to deployment, and expandable in a second configuration. The system may include a suction source for drawing tissue at the implant location into the suction cup of the delivery tool that is disposed at the distal portion. The delivery angle of the lead tip is based on the interior cavity of the suction cup rather than the angle of insertion with the suctioned tissue.

5 Claims, 10 Drawing Sheets

(51) Int. Cl.
   *A61B 17/34*   (2006.01)
   *A61B 18/00*   (2006.01)
   *A61B 17/00*   (2006.01)
   *A61B 17/30*   (2006.01)
   *A61N 5/06*    (2006.01)

(52) U.S. Cl.
   CPC ... *A61B 2018/00291* (2013.01); *A61N 1/0592* (2013.01); *A61N 2005/0649* (2013.01)

(58) Field of Classification Search
   CPC ........... A61B 2018/00351; A61B 2018/00357; A61B 2018/1495
   See application file for complete search history.

(56) References Cited

U.S. PATENT DOCUMENTS

| | | |
|---|---|---|
| 6,231,585 B1 | 5/2001 | Takahashi et al. |
| 6,613,062 B1 | 9/2003 | Leckrone et al. |
| 6,918,908 B2 | 7/2005 | Bonner et al. |
| 7,162,309 B2 | 1/2007 | Laske et al. |
| 7,241,358 B2 | 7/2007 | Gerlach |
| 7,801,622 B2 | 9/2010 | Camps et al. |
| 2007/0010793 A1* | 1/2007 | Callas ............... A61B 17/3478 604/500 |
| 2008/0051864 A1 | 2/2008 | Callas et al. |
| 2009/0187074 A1* | 7/2009 | Saadat ............... A61B 1/00085 600/114 |
| 2010/0030327 A1 | 2/2010 | Chatel |

\* cited by examiner

METHOD AND SYSTEM FOR LEAD DELIVERY

FIELD

The present disclosure pertains to systems, devices and method for accessing an anatomic surface, muscle layer, vessel or anatomic space of the body and particularly for accessing the pericardium to deliver a cardiac lead to the epicardial surface of the heart in a minimally invasive manner.

BACKGROUND

Implantable medical device (IMD) systems used for monitoring cardiac signals or delivering electrical stimulation therapy often employ electrodes implanted in contact with the heart tissue. Such electrodes may be carried by transvenous leads to facilitate implantation at endocardial sites or along a cardiac vein. Epicardial leads, on the other hand, carry electrodes adapted for implantation at an epicardial site. In past practice, placement of transvenous leads is often preferred by a physician over epicardial lead placement since transvenous leads can be advanced along a venous path in a minimally invasive procedure. Epicardial lead placement has generally required a sternotomy in order to expose a portion of the heart to allow implantation of the epicardial electrode at a desired site.

However, depending on the particular application, an epicardial lead may provide better therapeutic results than a transvenous lead. For example, in cardiac resynchronization therapy (CRT), a transvenous lead is advanced through the coronary sinus into a cardiac vein over the left ventricle. Implantation of a transvenous lead in a cardiac vein site can be a time-consuming task and requires considerable skill by the implanting clinician due to the small size and tortuosity of the cardiac veins. Furthermore, implant sites over the left heart chambers are limited to the pathways of the accessible cardiac veins when using a transvenous lead, which does not necessarily correspond to therapeutically optimal stimulation sites. Epicardial electrodes are not restricted to the pathways of the cardiac veins and can be implanted over any part of the heart surface. In order to take full advantage of cardiac stimulation therapies such as CRT, it is desirable to offer a cardiac lead that can be implanted in an epicardial location and a delivery system that allows the lead to be implanted using a generally less invasive approach, such as a mini-thoracotomy, a sub-xyphoid, or thorascopic approach, than a full sternotomy.

Helical fixation members for screwing into myocardial tissue are employed in epicardial pacing and defibrillation leads and the construction of such medical electrical leads are well known in the art. Typically the helical member terminates a distal end of the lead and serves as a stimulating electrode. A need remains for improvements to the delivery mechanisms to facilitate delivery of the distal member of the lead, such as a helix, for fixation of the lead to the epicardial surface of the heart.

SUMMARY

One factor contributing to proper placement of an implantable medical lead is the delivery angle of the distal lead end. However, the tortuous vasculature and interior body cavities make it challenging to ensure the distal lead end achieves a desired angle of intersection with the tissue during placement.

An implantable medical device delivery system includes a delivery tool having an elongate body coupled to a suction cup at a distal portion of the body. The elongate body has one or more lumens that extend from a proximal portion to the distal portion of the body. One or more of the lumens are provided in fluid communication with an interior cavity of the suction cup.

In one embodiment, the suction cup is configured to have a first cross-sectional profile prior to deployment of the delivery tool and a second cross-sectional profile subsequent to deployment. The first cross-sectional profile defines a narrower length in comparison to the second cross-sectional profile.

In some embodiments, the IMD system further includes a sheath having a circumference configured to receive the delivery tool with the suction cup being in the first cross-sectional profile. The delivery tool may be advanced distally through the sheath to a distal opening of the sheath. In response to advancing the delivery tool past the distal opening, the suction cup transitions to the second cross-sectional profile.

The IMD system may further include a vacuum source that couples to the proximal portion of the delivery tool for application of suction at the suction cup via the lumen. The suction force draws tissue inward into the internal cavity of the suction cup.

In accordance with the present disclosure, the angle of delivery of the medical lead is not dependent on the angle of intersection of the delivery channel lumen with the tissue. Rather, the delivery angle is defined by the interior cavity of the suction cup which thereby facilitates the placement of the lead at any desired angle on the implantation site.

The foregoing summary information is intended to merely illustrate some of the aspects and features of the present disclosure and is not meant to limit the scope in any way. In fact, upon review of the foregoing and the following described and depicted embodiments, one of skill in the art will surely recognize insubstantial modifications or extensions of the disclosure each of which is expressly intended to be covered hereby.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

The present disclosure is directed to delivery systems, devices and methods that facilitate placement of a medical lead in or on an anatomic space or organ (e.g. heart) of a patient. Among other things, the delivery device facilitates improvements in navigation of the lead during implant while optimizing the placement of the lead. The delivery device engages tissue at an implant site to define a desired intersection angle between the medical lead and the tissue. The delivery device provides at least a first cross-sectional profile that facilitates maneuverability of the device through the body to the implant site.

Figure 1:
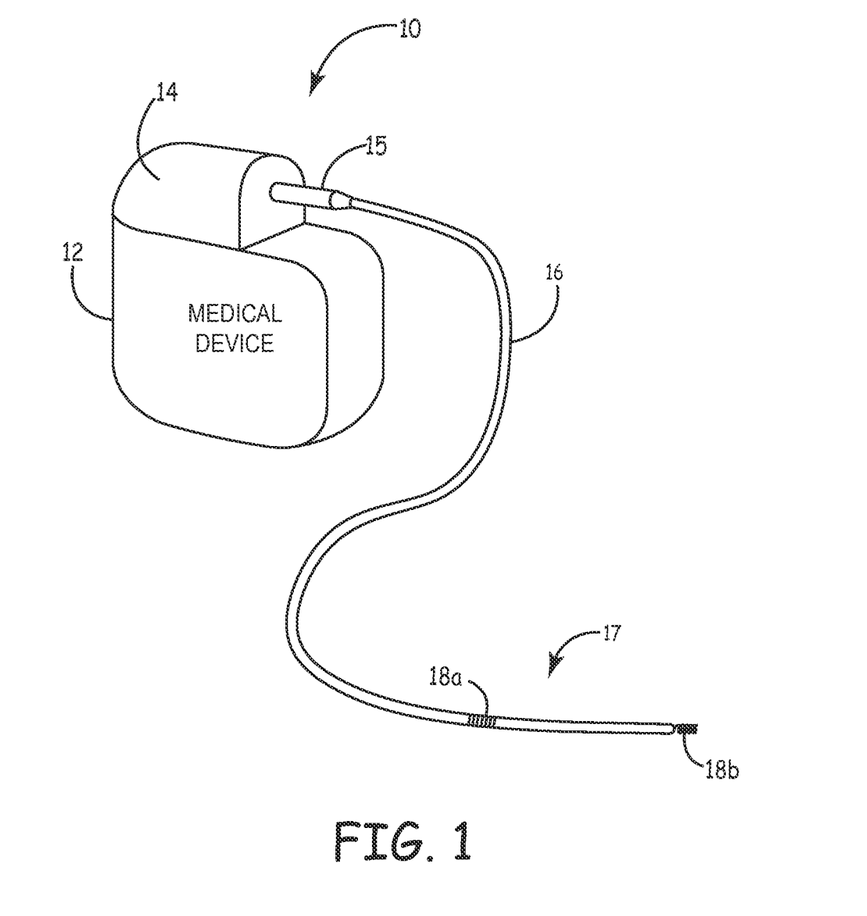
FIG. 1 depicts a medical device system.

FIG. 1 depicts a medical device system 10. The medical device system 10 includes a medical device housing 12 having a connector module 14 that electrically couples various internal electrical components of medical device housing 12 to a proximal end 15 of a medical lead 16. Medical device system 10 may comprise any of a wide variety of medical devices that include one or more medical lead(s) 16 and circuitry coupled to the medical lead(s) 16. An exemplary medical device system 10 may take the form of an implantable cardiac pacemaker, an implantable cardioverter, an implantable defibrillator, an implantable cardiac pacemaker-cardioverter-defibrillator (PCD), a neurostimulator, or a muscle stimulator. Medical device system 10 may deliver, for example, pacing, cardioversion or defibrillation pulses to a patient via electrodes 18 disposed on distal end 17 of one or more lead(s) 16. In other words, lead 16 may position one or more electrodes 18a, 18b (collectively "18") with respect to various tissue (e.g. cardiac tissue etc.) locations so that medical device system 10 can deliver pulses to the appropriate locations.

Lead 16 is provided with an elongated insulative lead body (e.g. insulative polymeric tube etc.), which carries a coiled conductor therein. Other lead body types may be substituted within the context of the present disclosure, including lead bodies employing multiple lumen tubes and/or stranded or braided conductors as disclosed in U.S. Pat. No. 5,584,873 issued to Shoberg et al. Alternatively, the lead may include additional conductors arranged either within a multi-lumen lead body or concentrically, as disclosed in U.S. Pat. No. 4,355,646 issued to Kallok et al. Additional pacing electrodes, sensors, or defibrillation electrodes, may of course be added to the lead body and coupled to additional conductors.

At the proximal end of the lead body is a connector assembly (e.g. industrial standard (IS)-1, IS-4 connector assemblies etc.) used in commercially available cardiac pacing leads. The connector assembly includes a conductive connector pin which is coupled by means of the conductor within the lead body to a tip electrode located at the distal tip of lead 16.

Figure 2:
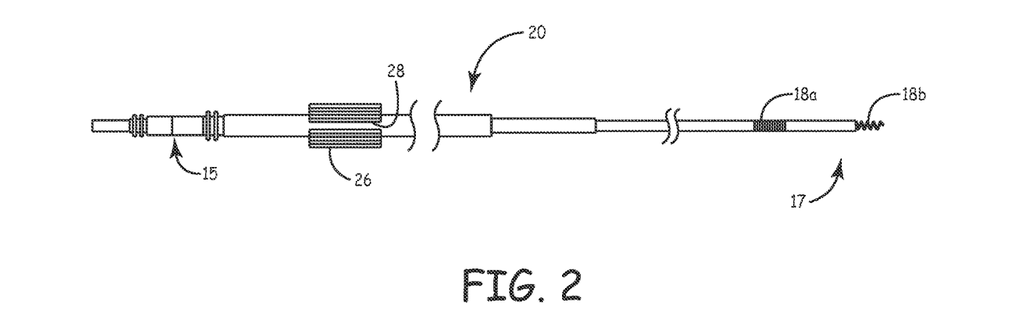
FIG. 2 is a plan view of medical electrical lead in accordance with one embodiment of the present disclosure.

FIG. 2 is a plan view of medical electrical lead 16 in accordance with one embodiment of the present disclosure. Lead 16 is adapted for implantation at epicardial locations, but may also be implanted transvenously in endocardial locations, including positions along the coronary sinus and cardiac veins. The lead 16 is a bipolar lead provided for sensing cardiac signals and delivering bipolar electrical stimulation pulses to the heart. In other embodiments, lead 16 may be provided as a unipolar lead or a multipolar lead. The lead 16 includes an elongated lead body 20 having proximal end 15 and distal end 17.

In one embodiment, a tip electrode 18b is provided as an active fixation electrode positioned at the distal end 17. An anode electrode 18a is spaced proximally from the tip electrode 18b and is provided as a flexible electrode formed from a coiled conductive wire, cable, or multifilar conductor. Tip electrode 18b is shown as a "screw-in" helical electrode and is used as the cathode electrode during bipolar stimulation. Helical tip electrode 18b is generally provided with a length that is relatively longer than helical tip electrodes carried by conventional transvenous leads. For example, a conventional transvenous helical tip electrode is commonly provided with a length of about 2 mm. In one embodiment of the present disclosure, tip electrode 18b is provided with a helix length greater than about 2 mm, for example a length of about 4 mm, to promote reliable fixation of the electrode 18b at an implant site.

Rotation of lead 16 may be facilitated by a rotation sleeve 26 adapted to be positioned around lead body 20. Rotation sleeve 26 is a generally cylindrical member, typically formed from plastic, such as silicone rubber or polyurethane, and having an open side 28 which may be widened to allow rotation sleeve 26 to be placed over lead body 20. Rotation sleeve 26 enables the implanting physician to more easily grip and rotate the lead during an implantation procedure. Rotation sleeve 26 is removed from lead body 20 after lead 16 is implanted.

Figure 3A:
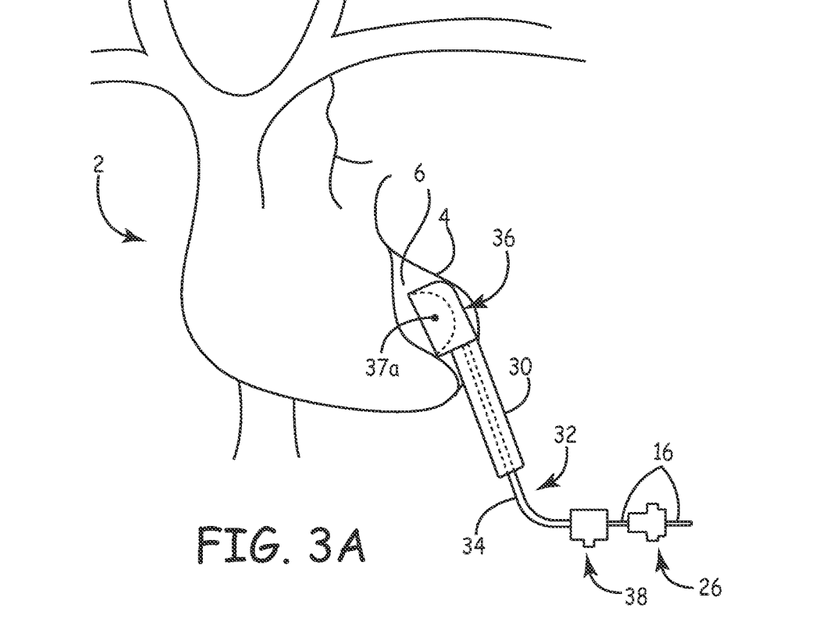
FIGS. 3A and 3B illustrate alternative schematics of delivery systems according to the present disclosure being positioned on an epicardial surface of a heart.
Figure 3B:
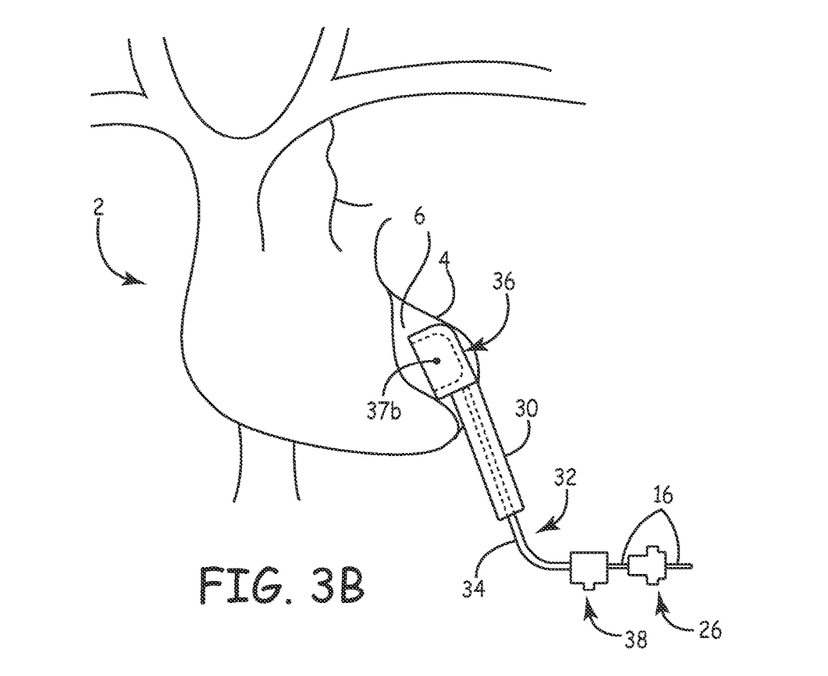

FIGS. 3A and 3B illustrate alternative schematics of delivery systems according to the present disclosure being positioned on an epicardial surface of a heart 2. A sheath 30, such as that of a guide catheter, is illustrated inserted through a pericardial sac 4 surrounding the heart 2. The illustration further depicts a partial cut-away view of heart 2. According to one method, sheath 30 is positioned over a guide wire that has been inserted into the pericardial space, for example from a sub-xyphoid position. The techniques associated with such a method are known to those skilled in the art and include those described in U.S. Pat. Nos. 4,991,571 and 5,336,252. FIG. 3 further illustrates a lead delivery tool 32 including a tool body 34, positioned within sheath 30. Lead delivery tool 32 further includes a suction cup 36. The suction cup 36 may be formed with the interior wall defining an interior cavity 37a, 37b (collectively "37"). In an exemplary embodiment of FIG. 3A, the interior wall of suction cup 36 defines an arcuate, concave-shaped interior cavity 37a. In the alternative embodiment of FIG. 3B, the interior wall of suction cup 36 may be formed to define a tubular-shaped interior cavity 37b. The suction cup 36 defines a distal opening that exposes the interior cavity to the exterior and one or more proximal openings that are coupled to respective one or more channels or lumens (FIG. 5) of lead delivery tool 32. As such, application of a suction force from a suction device coupled to the lead delivery tool 32 can be applied through the distal portion of suction cup 36.

Suction may be provided by the standard suction available in the operating room. The suction source may be coupled to suction cup 36 with a buffer flask. Alternatively, suction, may be provided via a manual or electric pump, a syringe, a suction or squeeze bulb or other suction or vacuum producing means, device or system. The suction source may comprise one or more vacuum regulators, valves, e.g., vacuum releasing valves, conduits, lines, tubes and/or hoses. The suction cup 36 is coupled to tool body 34 at a distal portion of the tool body 34.

Although the lead delivery tool 32 is illustrated as being delivered through sheath 30, delivery tool 32 may be delivered directly over the aforementioned guide wire without the need for sheath 30. The delivery tool 32 may be steered via a handle 38, attached near a proximal end of tool body 34, to orient the distal end of lead 16 for epicardial fixation.

Tissue that is adjacent to suction cup 36 at the implant location is suctioned during delivery of the lead. The angle of intersection of the lead with the suctioned tissue determines the delivery angle for fixation of the lead 16. The suction cup 36 may, in one embodiment, be an integral part of lead delivery tool 32. Alternatively, suction cup 36 may be formed separately but assembled to be in fluid communication with the body 34 of lead delivery tool 32. Lead 16 may be inserted into a lumen of lead delivery tool 32 either before or after suction cup 36 is placed in contact with tissue at the implant site. Suction cup 36 is oriented such that the helix electrode 18b terminating at a distal end of lead 16 is directed at a desired delivery angle in relation to an epicardial surface 6 for fixation.

In alternative embodiments, the lead delivery tool 32 may be positioned on heart 2 via a mini-thoracotomy wherein pericardial sac 4 has been excised according to techniques known to those skilled in the art of cardiac surgery.

Figure 4A:
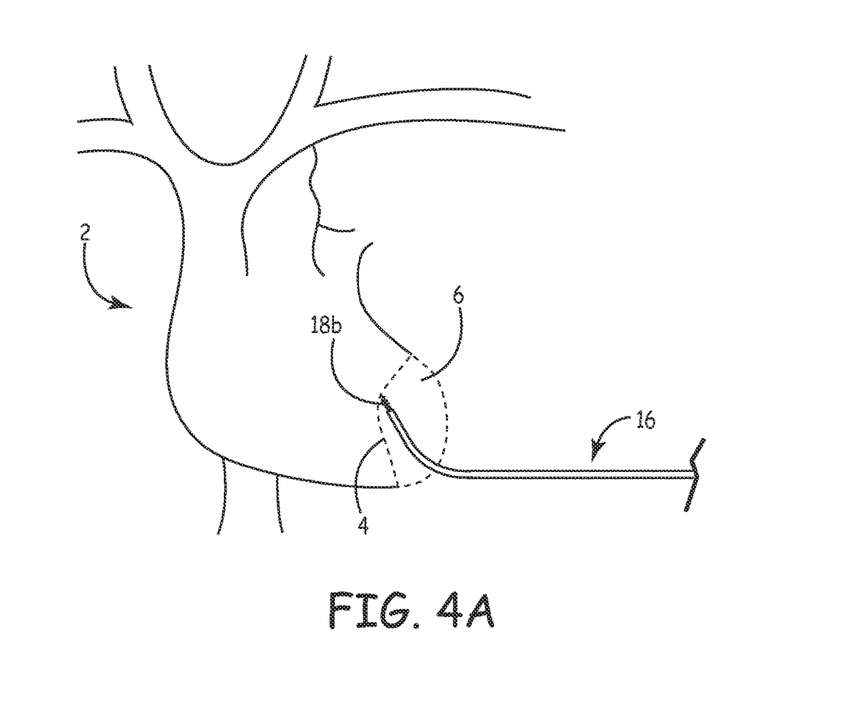
FIGS. 4A and 4B depict schematic views of a partial cutaway of the heart with a lead being advanced into the heart tissue in accordance with the delivery systems of the alternative embodiments of FIGS. 3A and 3B, respectively.
Figure 4B:
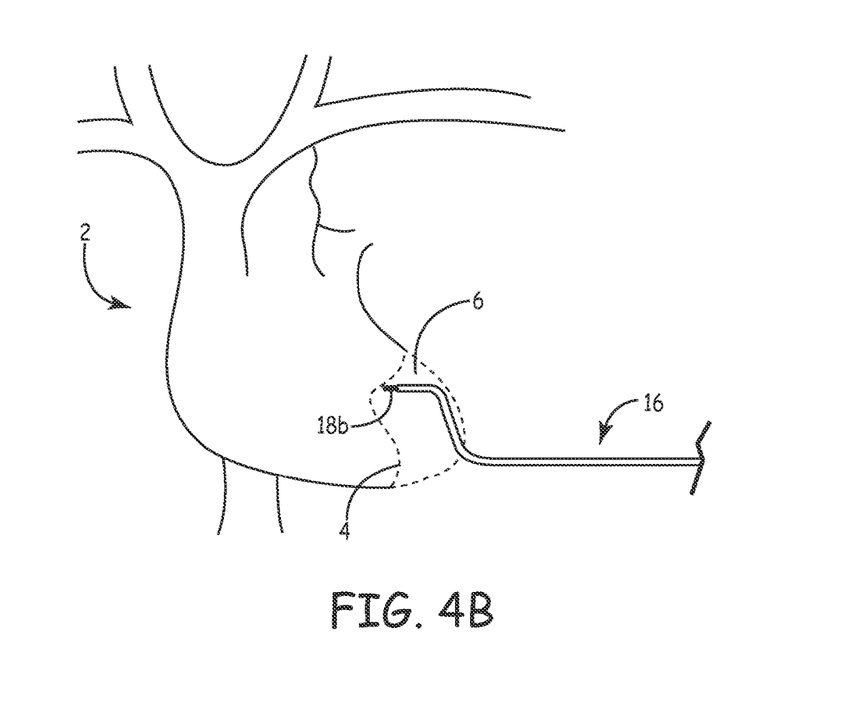

FIGS. 4A and 4B depict schematic views of a partial cutaway of heart 2 with the lead 16 being advanced into the heart tissue in accordance with the delivery systems of the alternative embodiments of FIGS. 3A and 3B, respectively. The illustrations depict the lead 16 subsequent to the suctioned tissue being released after fixation of the distal lead end. As shown in FIGS. 4A and 4B, the resulting angle of insertion and implantation of the distal lead end into the tissue is influenced by the geometry of the interior wall of suction cup 36. In FIG. 4A, a portion of the distal lead end including the helical element 18b is implanted at an angle relative to the plane of the tissue surface of heart 2. In accordance with the embodiment of FIG. 4B, the distal lead end including fixation element 18b is implanted at an angle that approximates a right angle in relation to the surface of heart 2.

Figure 5:
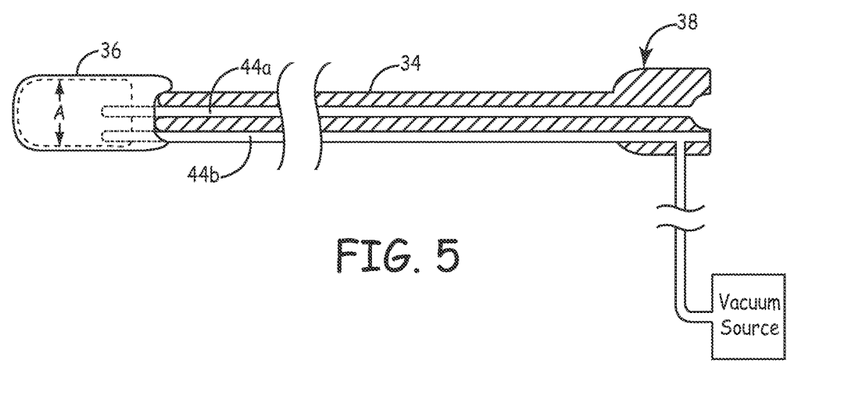
FIG. 5 is a plan view of a lead delivery system in a pre-deployment configuration of the lead delivery tool in accordance with one embodiment.

FIG. 5 is a plan view of a lead delivery system in a pre-deployment configuration of the lead delivery tool 32 in accordance with one embodiment. For ease of illustration, the sheath 30 is not shown in FIG. 5 although it should be understood that the sheath 30 may be used in accordance with some embodiments of this disclosure during implantation of the lead.

The delivery tool 32 includes the tool body 34 that extends from a proximal end 40 to a distal end 42. The tool body 34 is an elongate component that is dimensioned to fit within the vasculature, but also other body cavities (such as pericardial space) of a human body for implants that are performed through the vasculature. The tool body 34 may be a flexible component including one or more lumens 44a, 44b (collectively "44") that traverse the length of the body. In other embodiments, the tool body 34 may be a rigid or stiff member. The one or more lumens 44 may extend between one or more proximal opening(s) located proximate to the proximal end 40 to one or more respective distal opening(s) located proximate to the distal end 42. The tool body 34 is coupled to suction cup 36 at a distal portion of the tool body 34.

The suction cup 36 includes proximal openings 46a, 46b (collectively "46") such that when coupled to the tool body 34, the proximal opening 46 provides a continuous flow path for fluid and/or a lead advanced through the lumen 44. Suction cup 36 may be formed integrally with tool body 34, while in an alternate embodiment, the suction cup 36 and the tool body 34 are formed as separate components that are assembled together subsequent to formation. The suction cup 36 is formed into a hollow member to define, for example, a cup-shaped geometry having an opening that exposes an interior cavity of the hollow member to the exterior.

The suction cup 36 may have a length of about 10-16 millimeters (mm), a width of about 10-12 mm and a height of about 5-8 mm. The suction cup wall may have a thickness of about 2 mm. In other embodiments, the suction cup wall is formed from a dual layer such a gap is provided between the inner layer and the outer layer.

The lumen 44 of the tool body 34 terminates within an interior cavity of the suction cup 36. In other words, the lumen 44 is in fluid communication with the interior cavity of suction cup 36. As used in this disclosure, the phrase "in fluid communication" refers to a path for passage of an object (e.g., gas, or water but also including a solid member) from a first region or location to a second region or location. In accordance with this disclosure, the lumen 44 is in fluid communication with the interior cavity to provide a path for advancing a lead into the interior cavity or for exerting a suction force at the interior cavity of suction cup 36.

The tool body 34 is made from a biocompatible, thermoplastic material having requisite strength, malleability, flexibility and maneuverability. The material may also be one that permits slitting along a length of the body. For example, tool body 34 may be constructed of a polymeric material, such as polyether block amide, nylon block polymer, silicone, or polyurethane, stainless steel as well as composites or mono-polymers. An example of one suitable polymeric material is the polyether block amide marketed under the trademark PEBAX® and commercially available from Atofina Chemicals Inc., of King of Prussia, Pa. For construction of the suction cup 36, materials such as polyurethane, silicone rubber, stainless steel and plastic-based materials including Teflon®, Delrin®, Polyvinyl chloride (PVC), Poly (methyl methacrylate) (PMMA), polyethylene (PE) and polycarbonate or a combination of these materials may be employed. In other embodiments, shape memory materials including shape-memory polymers and metals such as nickel-titanium ("Nitinol") alloys and the like may be used for construction of the suction cup 36 to achieve functionality consistent with embodiments of this disclosure.

Figure 6:
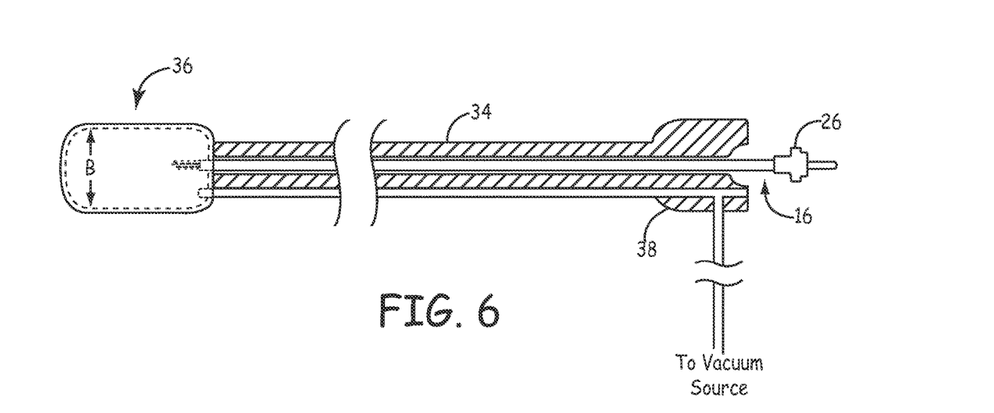
FIG. 6 is a plan view of a lead delivery system subsequent to deployment of the lead delivery tool in accordance with one embodiment.

FIG. 6 is a plan view of a lead delivery system subsequent to deployment of the lead delivery tool 32 in accordance with one embodiment. The suction cup 36 is deployed prior to the distal advancement of lead 16 through the distal end of the tool body 34 for placement. In one embodiment, deployment of the suction cup 36 may involve expansion of the suction cup 36 to define a predetermined internal cavity geometry.

As previously alluded to, the suction cup 36 is deployed prior to the lead being advanced for contact and fixation to the tissue. In particular, the suction cup 36 aids in fixating the lead 16 by drawing tissue into the internal cavity of the suction cup 36 to define a delivery angle that is determined by the suction cup geometry. In other words, the suction cup 36 may be deployed to its predetermined state so as to provide an interior cavity having a predetermined geometry. The delivery angle is therefore defined by the interior cavity rather than by the intersection angle of the tool body 34 to the tissue segment interfacing with the delivery tool 32.

As a consequence of utilizing the delivery tool 32 of the present disclosure, the angle of delivery of the medical lead 16 is not dependent on the angle of intersection of the distal lead tip with the tissue. This angle is deemed to be different than the angle that would result if the lead were fixed to the tissue without the tissue being suctioned into the interior cavity of the suction cup 36. Rather, the delivery angle is defined by the interior cavity of the suction cup 36 which thereby facilitates the placement of the lead 16 at any desired implantation site.

The suction cup 36 is placed on the desired implant site with the opening of the suction cup 36 facing the tissue. A suction force generated, for example, by a vacuum source is applied to the suction cup 36 through the lumen 44. The suction force draws the tissue towards and into the interior cavity of the suction cup 36. Subsequently, lead 16 may be advanced through lumen 44 distally toward the distal end of lead delivery tool 32 and into the interior cavity of the suction cup 36 to enable contact between the distal lead tip and the tissue. Actuation of rotation sleeve 26 facilitates the advancement of the helical lead tip 18b into the tissue.

Subsequent to fixation of the lead 16 to the tissue at the implant site, the suction force may be withdrawn to release the engaged tissue. Thereafter, the lead delivery tool 32 is withdrawn from the body.

Figure 7:
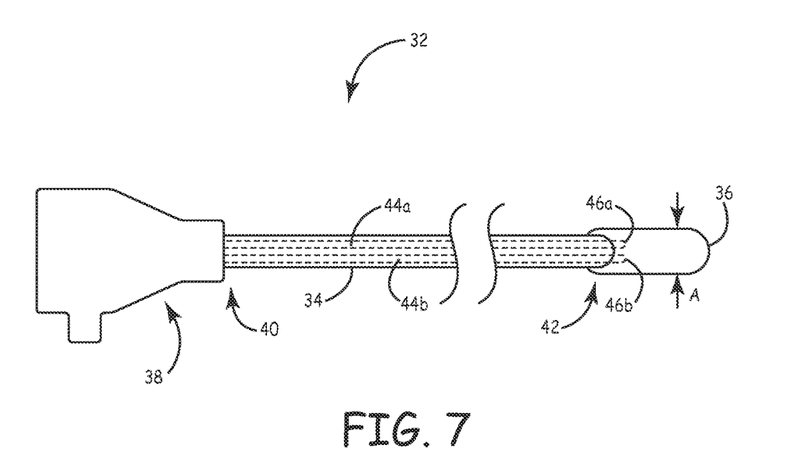
FIG. 7 is a cross-section of a plan view of an embodiment of the lead delivery tool.

FIG. 7 is a cross-section of a plan view of an embodiment of the lead delivery tool 32. The delivery tool 32 is shown in a pre-deployment configuration. The pre-deployment configuration refers to the state of the delivery tool 32 during navigation of the tool to the implant site. The pre-deployment configuration facilitates maneuverability of the delivery tool 32 through confined spaces within a patient's body for access to the desired organ e.g., heart.

As such, FIG. 7 illustrates suction cup 36 in a contracted or collapsed state as it would be presented (either as a standalone or within sheath 30) in a pre-deployment configuration. In the collapsed state, the outer wall of the suction cup 36 defines a narrower cross-sectional profile "A". The collapsible state facilitates the implantation of the lead by reducing the circumferential dimension of the lead delivery tool 32 that has to traverse the body or vasculature during navigation of the delivery tool to the implant location.

In one embodiment, the distal portion of delivery tool 32 may be contained within the tool body 34 in the pre-deployment state. As such, the suction cup 36 is contracted or retained within the tool body 34 to define the narrower cross-sectional profile. In another embodiment, the suction cup 36 may be collapsible onto itself or around the tool body 34 prior to the distal advancement of the lead to contact tissue at the implant location or fixation of the lead helical tip 18b to the tissue.

Figure 8:
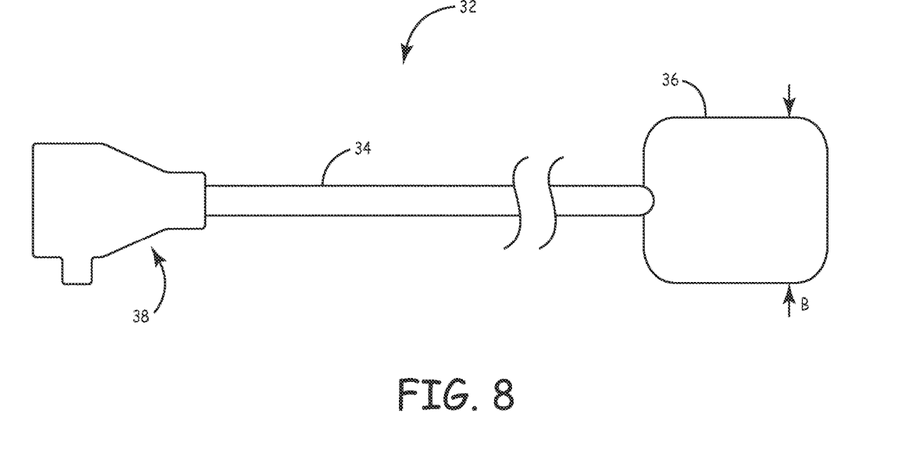
FIG. 8 is a cross-section of a plan view of another embodiment of the lead delivery tool.

FIG. 8 is a cross-section of a plan view of another embodiment of the lead delivery tool. The illustration depicts delivery tool 32 in a deployed configuration. The figure depicts the suction cup 36 having a wider cross-sectional profile "B", relative to that of the collapsed suction cup 36 in the pre-deployment state. This would occur, for example, subsequent to navigating the delivery tool 32 to the desired tissue site for advancement of the distal portion of lead 16 to fixate the lead to the tissue. The deployment may involve distally advancing the distal portion of the delivery tool 32 through the sheath 30 for expansion of the suction cup 36 to its predetermined shape.

The lumen 44 may be utilized to direct a fluid into an interior of the wall of suction cup 36. To facilitate the fluid controlled expansion, the suction cup 36 may have a dual layered wall, as described above, to provide a gap that holds the fluid that is directed therein. Alternatively, the suction cup 36 may have a dual-layer wall structure such that an inflatable border is defined between the two layers. Methods for construction of such balloon-like structures that are typically employed, for example, in catheters include catheters described in U.S. Pat. No. 7,727,228, which is incorporated herein by reference in its entirety.

In other embodiments, construction of the suction cup 36 with shape memory materials enables the exterior walls to transition from a first, pre-deployment, configuration to a second, deployed, configuration. The transition from the first configuration to the second configuration may occur in response to the delivery tool 32 being advanced from within the sheath 30. In other embodiments, the transition may occur due to a temperature phase change. Various methods are known for inducing the temperature change required to effect the shape-memory characteristic, including intervascular electrical resistive heating elements, R.F., and temperature-controlled fluid boluses injected through lumen 44. As such, the suction cup 36 would be held in a contracted state that maintains a first narrower circumferential dimension while the delivery tool 32 is within the sheath 30. Subsequent to being advanced distally of the sheath 30 distal end, the suction cup 36 relaxes to assume its predetermined shape that has a second circumferential dimension that is wider relative to the first dimension in the pre-deployed state.

Figure 9A:
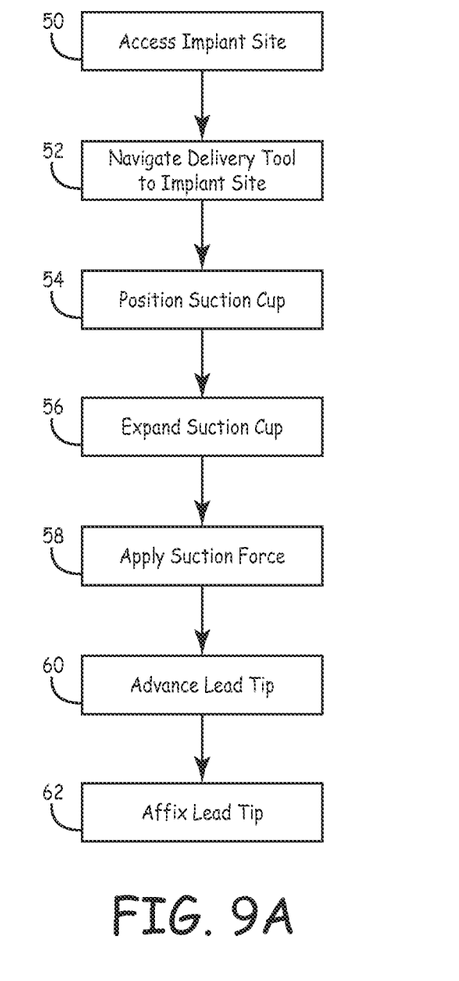
FIGS. 9A-B are flow charts illustrating steps included in alternate methods for implanting a lead using a delivery system according to the present disclosure.
Figure 9B:
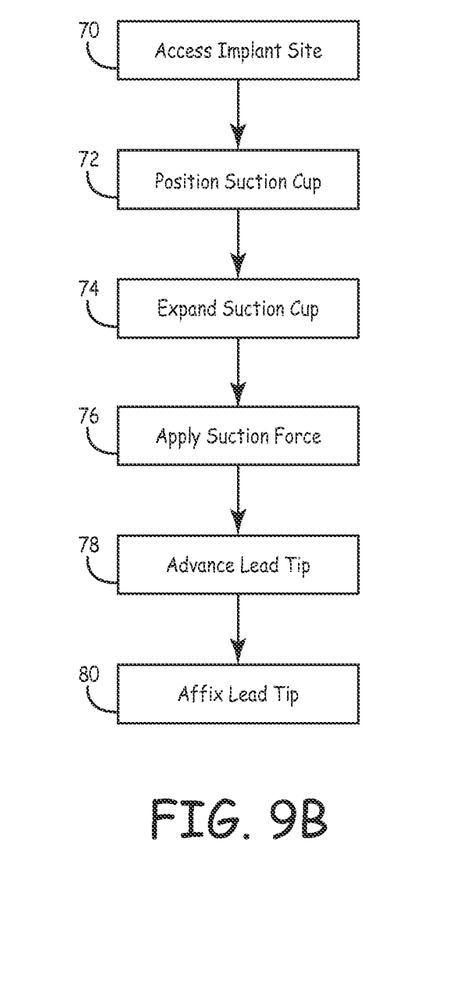

FIGS. 9A-B are flow charts illustrating steps included in alternate methods for implanting a lead using a delivery system according to the present disclosure. FIG. 9A shows steps associated with FIG. 3, while FIG. 9B shows steps associated with FIG. 4.

As described in conjunction with FIG. 3, one way of gaining epicardial access (50) is via a sub-xyphoid approach wherein a guide wire is passed into a space between pericardial sac 4 and epicardial surface 6. The lead delivery tool 32 is maneuvered to the implant site through, for example, distal advancement within the sheath 30 or through the vasculature perhaps by being passed over the aforementioned guide wire (52). The suction cup 36 is subsequently positioned in proximity to an epicardial implant site (54). Suction cup 36 is expanded to attain its predetermined shape (56) and define an interior cavity geometry. A suction force is applied to draw tissue into the interior cavity (58) so that a desired intersection angle between the distal portion of lead 16 and the tissue can be obtained based on the geometry of the interior cavity. Lead 16 is then advanced until helix 18b protrudes distally from the delivery tool body 34 (60). Once electrode 18b is in contact with epicardial surface 4, lead 16 is rotated, at a proximal end, to screw electrode 18b into epicardial surface 4 to affix to the tissue (62).

As described in conjunction with FIG. 4, another way of gaining epicardial access (70) is via a mini-thoracotomy followed by excision of pericardial sac 4. Suction cup 36 is then positioned in proximity to an epicardial implant site (72) and expanded to contact the tissue for fixation of electrode 18b (74). Once the suction force is applied (76), lead 16 is advanced until helix tip 18b protrudes distally from tool body 34 (78) and then lead 16 is rotated to screw helix 18b into epicardial surface 6 (80).

An epicardial delivery system according the present disclosure, fulfilling the functions described herein is not limited to the embodiments described herein. For instance additional embodiments of a lead delivery tool, such as delivery tool 32, include additional elongated shaft lumens to facilitate fluid delivery for flushing or drug delivery at an implant site or to carry a fiber optic bundle to facilitate visualization during implant manipulation.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable medical lead delivery system comprising:
    an elongate body having a proximal opening, a distal opening and a first continuous channel extending between the proximal opening and the distal opening;
    a suction cup coupled to the elongate body and having a third opening in fluid communication with the first continuous channel, wherein the third opening is in fluid communication with an internal cavity of the suction cup, wherein a suction force is applied to the internal cavity of the suction cup to draw in tissue at an angle defined by a geometry of the internal cavity;
    an implantable medical lead having a distal end that is advanced distally through the third opening of the suction cup to intersect tissue drawn into the internal cavity at the angle defined by the geometry of the internal cavity, wherein the suction cup is collapsible in a first configuration and expandable to define a substantially concave internal cavity in a second configuration; and
    a sheath, wherein the suction cup is disposed within a distal portion of the sheath in the first configuration and the suction cup is advanced distally from the sheath in the second configuration;
    wherein the suction cup transitions from the first configuration to the second configuration in response to the suction cup being distally advanced from within the sheath.

2. The implantable medical lead delivery system of claim 1, further comprising a second continuous channel in communication with the interior cavity of the suction cup and having a diameter configured to receive the implantable medical lead.

3. The implantable medical lead delivery system of claim 1, wherein the suction cup is slittable.

4. The implantable medical lead delivery system of claim 1, wherein the suction cup defines a first cross-sectional profile of the first configuration that is narrower than a second cross-sectional profile of the second configuration.

5. The implantable medical lead delivery system of claim 1, further comprising a vacuum source coupled to the proximal opening, wherein the suction cup draws tissue into the internal cavity in response to application of a suction force at the proximal opening.

* * * * *